United States Patent [19]

Laure

[11] 4,276,660
[45] Jul. 7, 1981

[54] CARPOMETACARPAL THUMB JOINT

[75] Inventor: George R. Laure, Kalamazoo, Mich.

[73] Assignee: Laure Prosthetics, Inc., Portage, Mich.

[21] Appl. No.: 42,706

[22] Filed: May 25, 1979

[51] Int. Cl.$^3$ .............................................. A61F 1/03
[52] U.S. Cl. ..................................... 3/1.91; 128/92 C
[58] Field of Search ..................... 3/1.9, 1.91, 1.911; 128/92 C

[56] References Cited

U.S. PATENT DOCUMENTS

| 3,651,521 | 3/1972 | Devas | 3/1.91 |
| 3,886,601 | 6/1975 | Findlay | 3/1.911 |
| 4,040,130 | 8/1977 | Laure | 3/1.91 |
| 4,059,854 | 11/1977 | Laure | 128/92 C X |

Primary Examiner—Clifford D. Crowder
Attorney, Agent, or Firm—Blanchard, Flynn, Thiel, Boutell & Tanis

[57] ABSTRACT

An endoprosthetic joint used to replace a dysfunctional thumb carpometacarpal joint comprises a first, or metacarpal, component adapted for insertion into the first metacarpal of the thumb and carrying thereon the ball portion of a ball-and-socket joint. In one embodiment, said joint further comprises a second or base portion of slightly flexible material defining a socket into which said ball is snappably received and having a projection thereon for reception into a suitably prepared recess in the trapezium bone of the hand. Both said components are cemented into place for firm holding therein. In a second embodiment, the metacarpal portion is identical with, and the base portion is generally similar to, that of the first embodiment. However, since with this embodiment the trapezium bone is removed, the base portion of said prosthesis is elongated whereby it may be received into a suitable recess in the navicular bone of the hand while still locating its socket adjacent the base of the first thumb metacarpal. The metacarpal portion of the joint in this embodiment is received into a suitably drilled hole in the first metacarpal of the thumb and the ball of said metacarpal component is snappably received into said socket in the same manner as in the above-discussed embodiment.

3 Claims, 7 Drawing Figures

CARPOMETACARPAL THUMB JOINT

FIELD OF THE INVENTION

The invention relates to a surgically implantable endoprosthetic carpometacarpal thumb joint and particularly to a type thereof in which the components may during the surgical process be first implanted into the appropriate bone structure and the joint then assembled by causing the parts thereof to be snapped together.

BACKGROUND OF THE INVENTION

In recent years, there has been a large amount of time and effort expended in the development of endoprosthetic joints of various kinds including such joints for replacement of various joints relating to the wrist and hand. This effort has manifested itself in a large volume of literature, both patent and otherwise, relating thereto. Much of this effort and resulting literature has, however, been directed toward joints relating to the wrist and fingers and a problem has continued to exist with respect to the thumb carpometacarpal joint. This is true in spite of the fact that said joint is an extremely common source of problems, such as arthritic problems, and is one of the most important joints of the entire hand for carrying out most manual manipulations. This problem appears to occur because of the relatively small bones in the hand adjacent the base of the thumb which have in the past appeared to preclude the successful anchoring of a prosthesis therein. For example, in U.S. Pat. No. 4,106,128, Greenwald et al, both the navicular and lunate bones of the hand, together with a portion of the capitate in the illustration shown with respect to the middle finger, are removed to provide room for the placement therein of the prosthesis with the base portion thereof being anchored in the radius bone. It is clear, however, from a mere inspection of the drawing in this patent that the middle finger is permitted to pivot at only one point and that this point is closely adjacent the radius bone rather than at the base of the finger itself. If this same treatment were applied to the thumb as suggested in said patent, the same problem exists, namely that the point of pivoting is too far from the base of the thumb to provide the desired natural motion.

Accordingly, the objects of the invention include:

1. To provide an endoprosthesis primarily intended for application to the thumb carpometacarpal joint which will closely simulate the movement of a natural joint.

2. To provide such a prosthesis which can be inserted between the trapezium and the first thumb metacarpal whereby the center of movement is at the natural position therefor adjacent the base of the thumb.

3. To provide a prosthesis, as aforesaid, which can be readily modified for use between the navicular and the first thumb metacarpal in those cases where the trapezium has disintegrated, with the center of movement of the joint still positioned at the natural point for same adjacent the base of the thumb.

4. To provide a prosthesis, as aforesaid, which will be simple to install by presently known techniques and may be so installed rapidly and efficiently.

5. To provide a prosthesis, as aforesaid, whose design embodies the maximum amount of presently known technology in order to secure long and successful operation thereof with a minimum of additional experimentation being required.

Other objects and purposes of the invention will be apparent to those acquainted with devices of this general type upon reading the following specification and inspection Zof the accompanying drawings.

DETAILED DESCRIPTION

Figure 1:
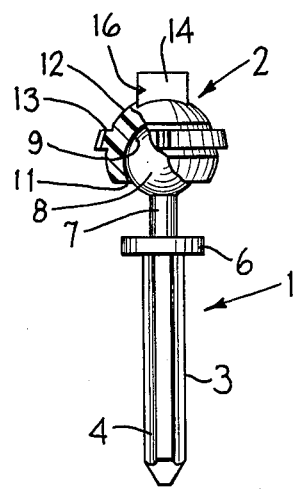
FIG. 1 is a side, partially sectional and partially broken, view of one preferred form of the invention, same being adapted for insertion between the first thumb metacarpal and the trapezium bone of the hand.

Concerning first the construction of the prosthesis, there is shown in FIG. 1 a metacarpal component 1 adapted for reception into the first thumb metacarpal bone and a base component 2 adapted for reception into a suitable recess provided in the trapezium bone.

Said metacarpal portion 1 comprises a pin portion 3 for reception into a hole suitably drilled into the first thumb metacarpal, said pin portion being preferably fluted as indicated at 4 to provent rotation of said carpal component within and with respect to the first metacarpal bone. A flange 6 is preferably provided at the end of said pin portion 3 for limiting the movement thereof into said bone and providing a stabilizing effect between said pin and said bone. A neck 7 extends coaxially with said pin beyond said flange 6 and carries at its end a ball 8 comprising one side of the joint as hereinafter further described. Said carpal component 1 will normally be made from a suitable bio-resistant metal of several known types, of which one preferred type is Vitallium (standard formulation ASTM F-75).

Considering now the base portion 2, same comprises a slightly resilient plastic material of several known types such as an ultra-high molecular weight polyethylene, such as that made by Ruhrchemie AG of Oberhausen, Germany, and sold under the trademark "Hostalen GUR No. 412". Same defines a recess 9 for the reception of the ball 8, said recess defining somewhat more than 180° of curvature in order to provide the lips 11 which assist in holding said ball within said recess. However, it will be recognized that the holding relationship provided in this manner is primarily to hold the parts in proper assembled position during the healing of the hand following surgery and that the muscles and ligaments are relied upon thereafter in the same manner as same hold together the bones of a normal hand.

Said base 2 in this embodiment is provided with a generally curved, as spherical, outer surface 12 for easy moldability thereof and also for easy fitting into an easily made recess in the trapezium but same may be of other shapes if preferred. A radially extending flange 13 is preferably provided for assisting in the seating and stabilizing of said base in and with respect to the trapezium. A short projection 14 extends from the base 2, radially of the recess therein, and is coaxial with the metacarpal component 1 when said base is symmetrically positioned with respect to said component 1. The projection 14 is preferably of non-circular, here square, cross section to insure against rotation thereof in and with respect to the trapezium and is further preferably provided with notches 16 at its corners to assist in gripping of the adhesive by which said base is adhered to the trapezium. If desired, further notches 17 may be provided in the flange 13 for the same purpose.

Figure 3:
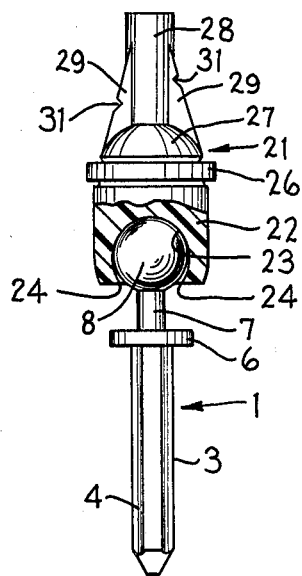
FIG. 3 is an elevational partially broken and partially sectional view of a modification of the prosthesis for use between the navicular bone and the first thumb metacarpal, the sectional portion being taken diametrically therethrough.
Figure 4:
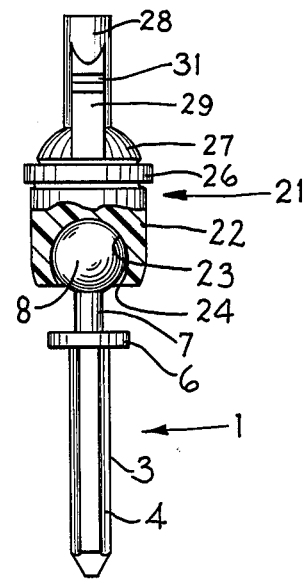
FIG. 4 is an elevational partially broken, partially sectional view taken in a direction perpendicular to the plane of FIG. 1, the sectional portion being taken diametrically therethrough.
Figure 2:
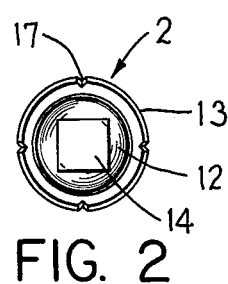
FIG. 2 is an end view of the prosthesis of FIG. 1 taken from the upper end thereof as shown in FIG. 1.

Turning now to the form of the invention shown in FIGS. 3 and 4, it may be noted first that the metacarpal portion thereof is identical with that shown in FIGS. 1 and 2 and hence said parts are identified by the same numbers as utilized in connection with FIGS. 1 and 2. The base portion, however, while generally similar, is in its details somewhat different. In FIGS. 3 and 4, the base portion comprises a plastic molding generally identified by the numeral 21 which may be of any plastics material such as that above identified in connection with FIGS. 1 and 2, which will slide smoothly against the metal used for the metacarpal portion 1, is slightly resilient, and which will be sufficiently biologically inert as to be neither absorbed nor rejected by a human body. Said base 21 has a cup portion 22 containing a recess 23 adapted for receiving the ball 8 of the metacarpal portion 1, said recess extending through an arc of more than 180% so as to provide lips 24 to assist in retaining the ball 8 in position. Said lips are, however, of sufficient flexibility that said ball is merely snapped into place at an appropriate time in the surgical procedure. The cup portion 22 preferably includes a flange 26 for the same purposes as the flange 13 above mentioned, has a contoured portion 27 of partially spherical shape for reception into a suitably and similarly shaped recess in the bone end into which this portion of the prosthesis is implanted, a projection 28 which is generally radial of the recess 23 and one or more fins 29 extending radially of the projection 28. Said fins both assist in retaining the projection 28 firmly into the bone member receiving same and prevent rotation thereof with respect to such bone. Notches 31 may be provided in said fins if desired to assist the adherence of adhesive used to fasten the prosthesis into the bone. The cup portion 22 is of a generally elongated cylindrical configuration, as shown in FIGS. 3, 4 and 7.

Figure 6:
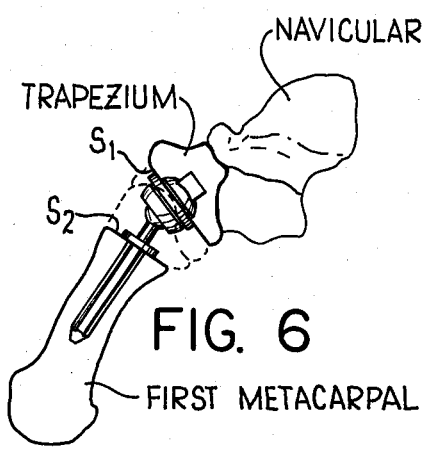
FIG. 6 is a somewhat schematic representation of hand bones showing the manner of installation thereinto of the form of the prosthesis shown in FIGS. 1 and 2.

The implanting of the prosthesis parallels procedures already known, which is one of the objects of the invention, but it also employs features of novelty which help to characterize the invention as will be brought out further hereinafter. In the case where an arthritic condition has not proceeded so far as to destroy or seriously weaken the trapezium, the form of the invention shown in FIGS. 1 and 2 may be employed. As shown in FIG. 6, the trapezium is somewhat squared off and a recess created therein for receiving the curved portion 12 of the base 2. The flange 13 bears against the squared-off surface $S_1$ to assist in holding said base portion firmly with respect to the bone comprising the remainder of the trapezium. A small portion of the first metacarpal is likewise removed as indicated by the broken lines in FIG. 6 and the remainder squared off to provide an essentially flat surface $S_2$ in FIG. 6. A suitable hole is drilled in said metacarpal for the reception of the pin portion 3 of the metacarpal component 1 and said metacarpal component 1 inserted and fixed by adhesive as shown in FIG. 6. Flange 6 bears against the surface $S_2$ for limiting the distance the pin 3 moves thereinto and also assists further in stabilizing same with respect to the first metacarpal bone. It will be noted further on inspection of FIG. 6 that the surfaces $S_1$ and $S_2$ are so positioned and selected with respect to the original bone that the center of movement between the ball 8 and the base member 2 is substantially at the center of movement provided between the components of the original joint. Thus, the muscles and ligaments not only hold the prosthesis firmly together but may operate in a natural and normal manner to produce a natural and normal thumb movement.

Figure 7:
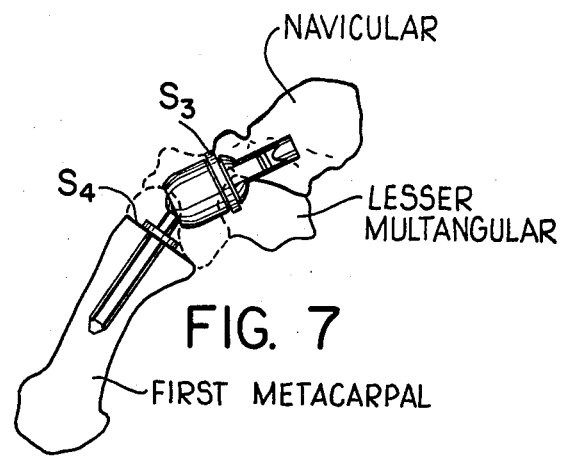
FIG. 7 is a somewhat schematic view of hand bones showing the manner of installation thereinto of the form of the prosthesis shown in FIGS. 3 and 4.
Figure 5:
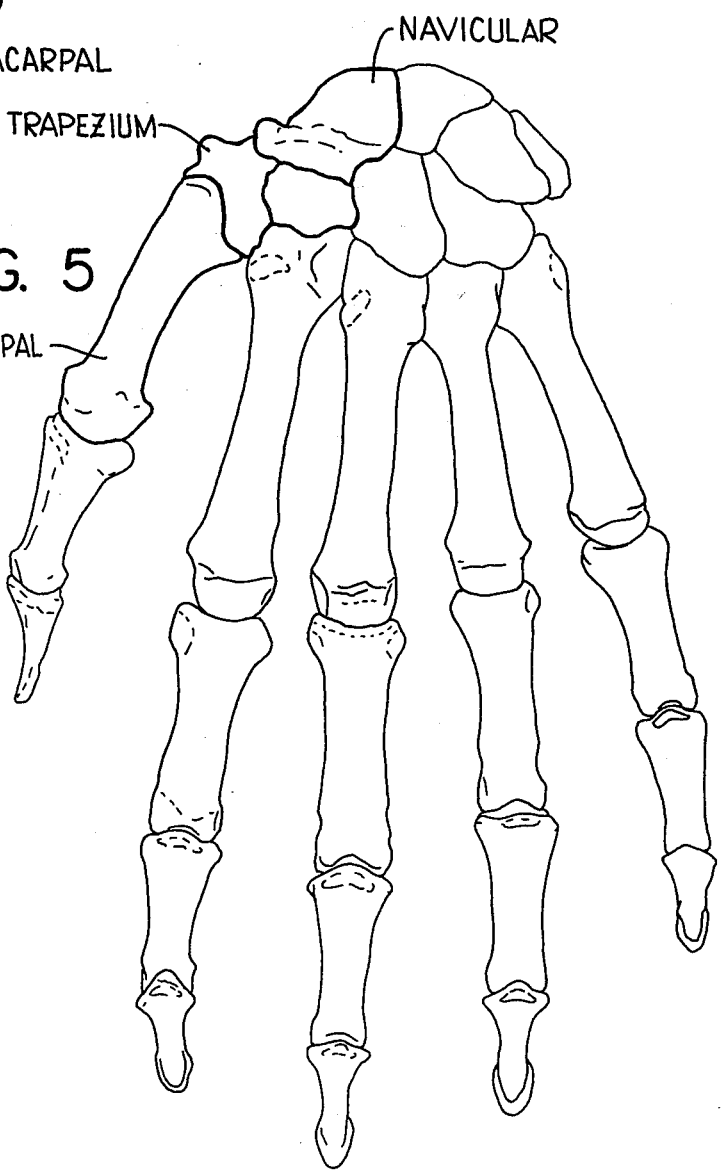
FIG. 5 is a somewhat schematic representation of the bones in the hand.

In the case where the trapezium is so weakened or destroyed by accident or disease, such as by arthritis, that it cannot be used in the manner illustrated in FIG. 6, same may be removed entirely and the form of the invention shown in FIGS. 3 and 4 then employed in the manner shown in FIG. 7. In this case, with the trapezium entirely removed, a portion of the navicular together with a portion of the adjacent lesser multangular will be reamed out and shaped for the reception of the curved portion 27 of the base 21 and a suitable opening drilled and cut for receiving the projection 28 and associated fins 29. The flange 26 is employed as previously both to limit the distance the projection 28 extends into the navicular and also to assist in stabilizing same with respect to such bone. The first metacarpal is squared off approximately in the same manner as previously and drilled the same as previously for the reception of the pin 3 of the metacarpal component 1. The length of the cup portion 22 of the base portion 21 is so determined, and the surfaces $S_3$ and $S_4$ so spaced from each other, that again in this embodiment the base 21 receives the ball 8 appropriately for positioning the center of movement therebetween at least approximately at the center of movement of the natural joint. Thus again the muscles and ligaments will function with respect to the hand and thumb in a normal manner and will produce a movement of the thumb with respect to the hand closely if not exactly simulating the natural movement of such parts.

It will be apparent that although the prosthesis will be made in different sizes in expectation of insertion into hands of different sizes, the surgeon may nevertheless obtain very accurate correlation between the joint of the prosthesis and the center of movement of the natural joint by exercising appropriate control over the trimming of the bone structure, and positioning of the surfaces $S_1$, $S_2$ and $S_3$, $S_4$.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In a surgically implantable endoprosthetic carpometacarpal thumb joint for connection between the first thumb metacarpal bone and an appropriate hand bone, such as the trapezium or the navicular, the improvement comprising:

a one-piece metacarpal component adapted to be fixedly implanted into the upper end of the first thumb metacarpal, said metacarpal component including an elongated pin adapted for reception substantially coaxially into the first thumb metacarpal, a flange fixed on said pin adjacent the upper end thereof for limiting the extent to which the pin can enter into the first thumb metacarpal, the flange being adapted to seat against a substantially flat surface formed on the first thumb metacarpal, a pinlike support fixed to said flange and projecting therefrom in the opposite direction from said pin, and a ball fixedly secured to said pinlike support at the free end thereof; and a one-piece base component for implanting into said appropriate hand bone, said base component including an enlarged base member constructed of a molded plastic and having a recess formed therein which opens outwardly through an opening formed in one end thereof, said recess defining a substantial portion of a sphere such that central sections through said recess define an arcuate extent in excess of 180°, said base member defining thereon a resilient lip in surrounding relationship to the opening into said recess for snappably receiving said ball directly within said recess and retaining same therein;

said one-piece base member also including a projection fixed to and projecting outwardly from the end thereof which is opposite from but approximately aligned with the recess opening, said projection having means associated therewith for permitting the projection to be nonrotatably implanted into said appropriate hand bone, said projection and said pin being substantially aligned with one another and with the center of said recess when the metacarpal and base components are positioned in a substantially straight positional relationship;

said one-piece base component further including a flange fixed to and projecting outwardly from said base member for limiting the extent of movement thereof into the appropriate hand bone, said flange seating against a substantially flat surface formed on said hand bone for stabilizing said base member, and the base member at the end thereof opposite said recess opening being provided with an outwardly projecting contoured portion of partial spherical shape for reception into a suitably and similarly shaped recess formed in the appropriate hand bone, said contoured portion being positioned directly adjacent and projecting outwardly from the flange fixed to said base member, and said projection being fixed to and projecting centrally outwardly from said contoured portion;

said metacarpal and base components being adapted for reception respectively into said first thumb metacarpal and said appropriate hand bone at such respective depths thereinto that the center of rotation between said ball and said base member will be substantially coincident with the center of rotation of the preexisting thumb joint, and said ball and said recess both being of smooth spherical configurations to permit substantially universal swiveling of the ball within the recess so as to approximate the normal universal pivoting movement of the thumb relative to the hand.

2. A thumb joint according to claim 1, wherein said base member is formed substantially as a truncated hollow sphere, said recess opening inwardly of the sphere through the truncated end thereof and defining the hollow interior of said sphere, said projection being of noncircular cross section and having a length less than the diameter of said sphere and extending radially outwardly of said sphere in alignment with said recess but substantially diametrically opposite said truncated end, and said flange as fixed to said base member being disposed so as to encircle said truncated hollow sphere in the region thereof so that the flange encircles a part of said recess, the portion of said truncated hollow sphere which is located on the side of said last-mentioned flange opposite from said recess opening defining said contoured portion.

3. A thumb joint according to claim 1, wherein said appropriate bone is the navicular, wherein said projection is of substantial length for firm reception into an appropriate opening in said navicular, and wherein the base member is of a substantially elongated cylindrical configuration so as to enable the recess therein to be so spaced from the navicular as to be positioned substantially at the center of rotation of the preexisting thumb joint, the axial length of said base member being such that the recess projects into said base member from one end thereof for no more than approximately one-half of the overall length thereof, and the flange as fixed to said base member being positioned closely adjacent the end thereof opposite from the recess so that said flange does not directly encircle the recess.

* * * * *